(12) United States Patent
Huang et al.

(10) Patent No.: US 10,161,901 B2
(45) Date of Patent: Dec. 25, 2018

(54) DUAL GATE BIOLOGICALLY SENSITIVE FIELD EFFECT TRANSISTOR

(71) Applicant: TAIWAN SEMICONDUCTOR MANUFACTURING CO., LTD., Hsinchu (TW)

(72) Inventors: Yu-Jie Huang, Kaohsiung (TW); Jui-Cheng Huang, Hsinchu (TW); Cheng-Hsiang Hsieh, Taipei (TW)

(73) Assignee: Taiwan Semiconductor Manufacturing Co., Ltd. (TW)

( * ) Notice: Subject to any disclaimer, the term of this patent is extended or adjusted under 35 U.S.C. 154(b) by 72 days.

(21) Appl. No.: 14/961,588

(22) Filed: Dec. 7, 2015

(65) Prior Publication Data

US 2017/0160226 A1    Jun. 8, 2017

(51) Int. Cl.
*G01N 27/414* (2006.01)

(52) U.S. Cl.
CPC ..... *G01N 27/4145* (2013.01); *G01N 27/4148* (2013.01)

(58) Field of Classification Search
CPC ...... G01N 27/00; G01N 27/26; G01N 27/403; G01N 27/414; G01N 27/4145; G01N 27/4148; G01R 35/00; G01R 35/005; G01R 31/3191; G08B 29/20; G07D 2205/0012; H01L 29/0843; H01L 29/66431; H01L 29/76833; H01L 29/778; H01L 21/0617; H01L 21/8232; H01L 21/845; H01L 27/0705; H01L 27/085; H01L 27/105; H01L 27/11803; H01L 27/1211; H01L 27/14679; H01L 27/228; H01L 27/2454; H01L 27/283
(Continued)

(56) References Cited

U.S. PATENT DOCUMENTS

| | | |
|---|---|---|
| 5,702,981 A | 12/1997 | Maniar et al. |
| 6,639,841 B2 * | 10/2003 | Chen .................. G11C 11/5621 |
| | | 365/185.18 |

(Continued)

FOREIGN PATENT DOCUMENTS

| | | |
|---|---|---|
| JP | 2008-176243 | 1/2007 |
| KR | 10-20120121228 | 11/2012 |
| KR | 10-20130078182 | 7/2013 |

OTHER PUBLICATIONS

D. Y. Chen et al., "An Intelligent ISFET Sensory System With Temperature and Drift Compensation for Long-Term Monitoring", IEEE Sensors Journal, vol. 8, No. 12, Dec. 2008.
(Continued)

*Primary Examiner* — Hoai-An D. Nguyen
(74) *Attorney, Agent, or Firm* — Sterne, Kessler, Goldstein & Fox P.L.L.C.

(57) ABSTRACT

A biologically sensitive field effect transistor includes a substrate, a first control gate and a second control gate. The substrate has a first side and a second side opposite to the first side, a source region and a drain region. The first control gate is disposed on the first side of the substrate. The second control gate is disposed on the second side of the substrate. The second control gate includes a sensing film disposed on the second side of the substrate. A voltage biasing between the source region and the second control gate is smaller than a threshold voltage of the second control gate.

20 Claims, 8 Drawing Sheets

(58) Field of Classification Search
USPC ........ 324/600, 601, 202, 750.02, 130, 76.11, 324/500, 537, 762.01, 762.09; 702/85; 257/9, 20, 27, 192, 213, 216, E21.623, 257/E21.637
See application file for complete search history.

(56) References Cited

U.S. PATENT DOCUMENTS

| | | | |
|---|---|---|---|
| 7,060,510 B2 | 6/2006 | Bonnell et al. | |
| 7,306,924 B2 | 12/2007 | Gomez et al. | |
| 7,632,670 B2 | 12/2009 | Offenhausser et al. | |
| 7,695,609 B2 | 4/2010 | Soundarrajan et al. | |
| 7,696,530 B2 | 4/2010 | Yamamoto et al. | |
| 7,833,708 B2 | 11/2010 | Enzelberger et al. | |
| 7,923,314 B2 | 4/2011 | Tezuka et al. | |
| 8,007,727 B2 | 8/2011 | Shalev et al. | |
| 8,420,328 B2 | 4/2013 | Chen et al. | |
| 8,471,559 B2 | 6/2013 | Taherian et al. | |
| 8,519,490 B2 | 8/2013 | Bikumandla | |
| 8,557,643 B2 | 10/2013 | Han et al. | |
| 8,728,844 B1 | 5/2014 | Liu et al. | |
| 8,778,269 B2 | 7/2014 | Joshi et al. | |
| 8,871,549 B2 | 10/2014 | Ellis-Monaghan et al. | |
| 8,878,258 B2 | 11/2014 | Monfray et al. | |
| 9,080,969 B2 | 7/2015 | Liu et al. | |
| 9,389,199 B2 | 7/2016 | Cheng et al. | |
| 9,417,209 B2 | 8/2016 | Shen et al. | |
| 9,459,234 B2* | 10/2016 | Kalnitsky | G01N 27/414 |
| 2008/0175061 A1* | 7/2008 | Kim | G11C 16/3418 365/185.18 |
| 2012/0007166 A1* | 1/2012 | Zhu | H01L 21/28273 257/319 |
| 2013/0200438 A1* | 8/2013 | Liu | G01N 27/414 257/253 |
| 2014/0252421 A1* | 9/2014 | Liu | H01L 29/66477 257/253 |
| 2014/0264467 A1 | 9/2014 | Cheng et al. | |
| 2014/0295573 A1 | 10/2014 | Huang et al. | |
| 2014/0368415 A1 | 12/2014 | Kim et al. | |
| 2015/0316503 A1* | 11/2015 | Hoque | H01L 29/78 257/253 |
| 2017/0102356 A1* | 4/2017 | Lin | G01N 27/4145 |

OTHER PUBLICATIONS

E. Muller et al., "Differential ISFET/REFET Pairs as a Reference System for Integrated ISFET-Sensorarrays", 1991IEEE, pp. 467-470, 1991.

David Welch et al., "Experimental and Simulated Cycling of ISFET Electric Fields for Drift Reset", IEEE Electron Device Letters, vol. 34, No. 3, Mar. 2013.

S. Casans et al., "Circuit provides constant current for ISFETs/MEMFETs", EDN, design ideas, Oct. 26, 2000.

P. Bergveld, "The Operation of an ISFET as an Electronic Device", Sensors and Actuators, 1 (1981) 17-29.

Arkadiy Morgenshtein et al., "A Microsystem for ISFET-Based pH Measurement in CMOS Technology", The 16th European Conference on Solid-State Transducers | Sep. 15-18, 2002, Prague, Czech Republic, pp. 360-363, 2002.

Notice of Allowance, dated Mar. 30, 2017, for Korean Intellectual Property Office Patent Appl. No. 10-2016-0027788, 3 pages, including translation.

Korean Office Action dated May 9, 2017, directed to related KR Application No. 10-2017-0018576, from the Korean Intellectual Property Office; 6 pages.

English language abstract of Japanese Patent Application No. 2007-012040 also known as Publication No. 2008-176243, Japanese Patent Office, accessed Apr. 24, 2017, listed as document FP2 on the accompanying form PTO/SB/08a; 1 page.

English language abstract of Korean Publication No. 10-2012-0121228, Korean Patent Office KIPRIS, accessed Apr. 24, 2017, listed as document FP1 on the accompanying form PTO/SB/08a; 1 page.

* cited by examiner

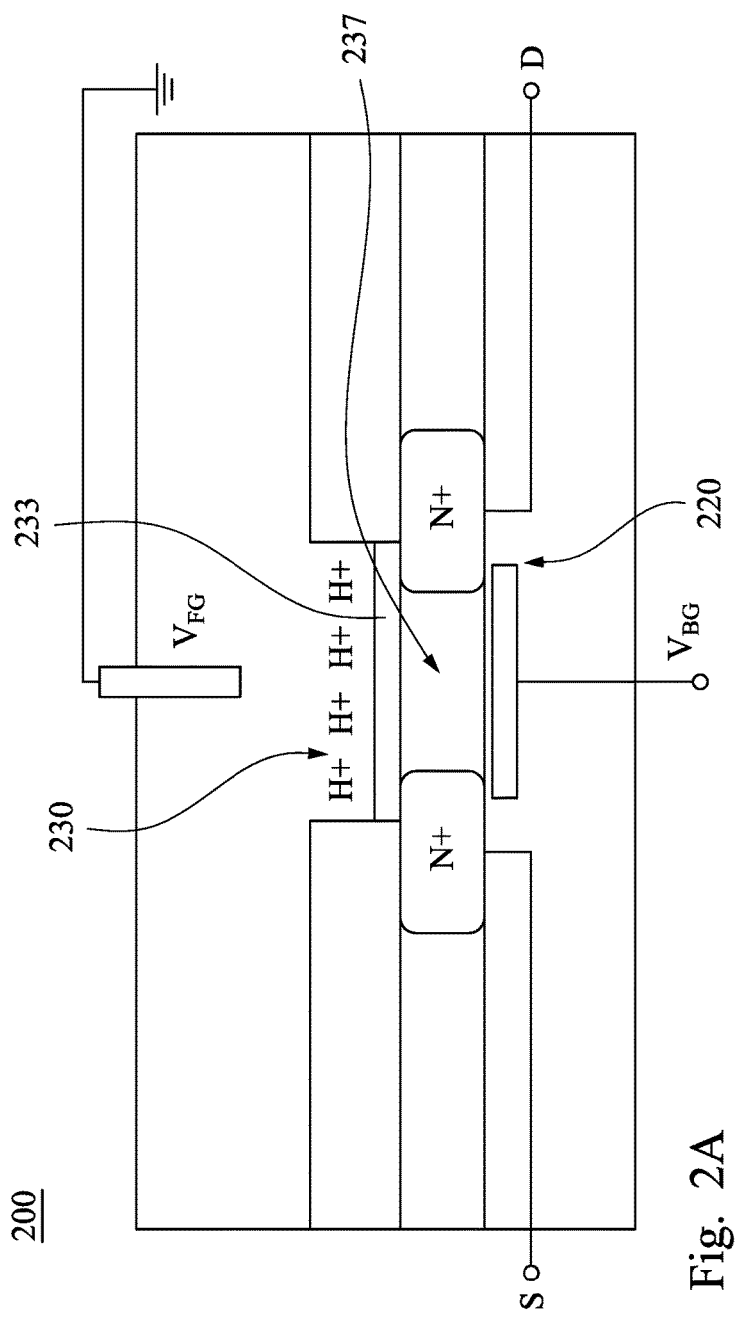
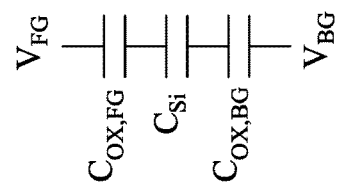
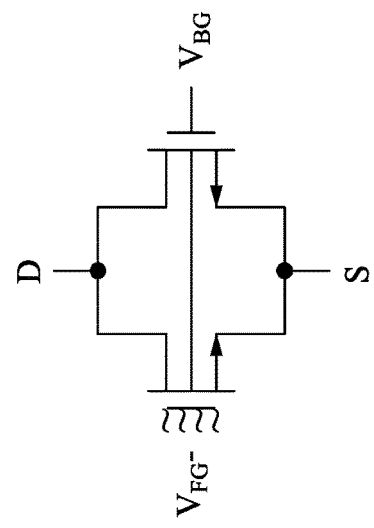
Fig. 2A
Fig. 2B
Fig. 2C

DUAL GATE BIOLOGICALLY SENSITIVE FIELD EFFECT TRANSISTOR

BACKGROUND

Biosensors are devices for sensing and detecting biomolecules and operate on the basis of electronic, electrochemical, optical and mechanical detection principles. Biosensors that include transistors are sensors that electrically sense charges, photons, and mechanical properties of bio-entities or biomolecules. The sensor detects the concentration of bio-entities or biomolecules, or through interaction and reaction between specified reactants and bio-entities/biomolecules. Such biosensors are fast in signal conversion and can be manufactured using semiconductor processes and easily applied to integrated circuits and MEMS.

A field effect transistor (FET) includes a source, a drain and a gate and may be used as a sensor for various types of targets. A biologically sensitive field effect transistor, or bio-organic field effect transistor, (Bio-FET) is created to detect biomolecules, including, for example, H+, Ca2+, DNA, proteins and glucose. An electrolyte containing the molecule of interest is used as the Bio-FET gate.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

FIG. 2A is a schematic cross-sectional diagram showing a dual gate biologically sensitive field effect transistor (Bio-FET) in accordance with some embodiments of the instant disclosure;

FIG. 2B is a schematic diagram showing a simplified circuit route of a dual gate biologically sensitive field effect transistor (Bio-FET) in accordance with some embodiments of the instant disclosure;

FIG. 2C is a schematic diagram showing a simplified circuit layout of a dual gate biologically sensitive field effect transistor (Bio-FET) in accordance with some embodiments of the instant disclosure;

DETAILED DESCRIPTION

Figure 1:
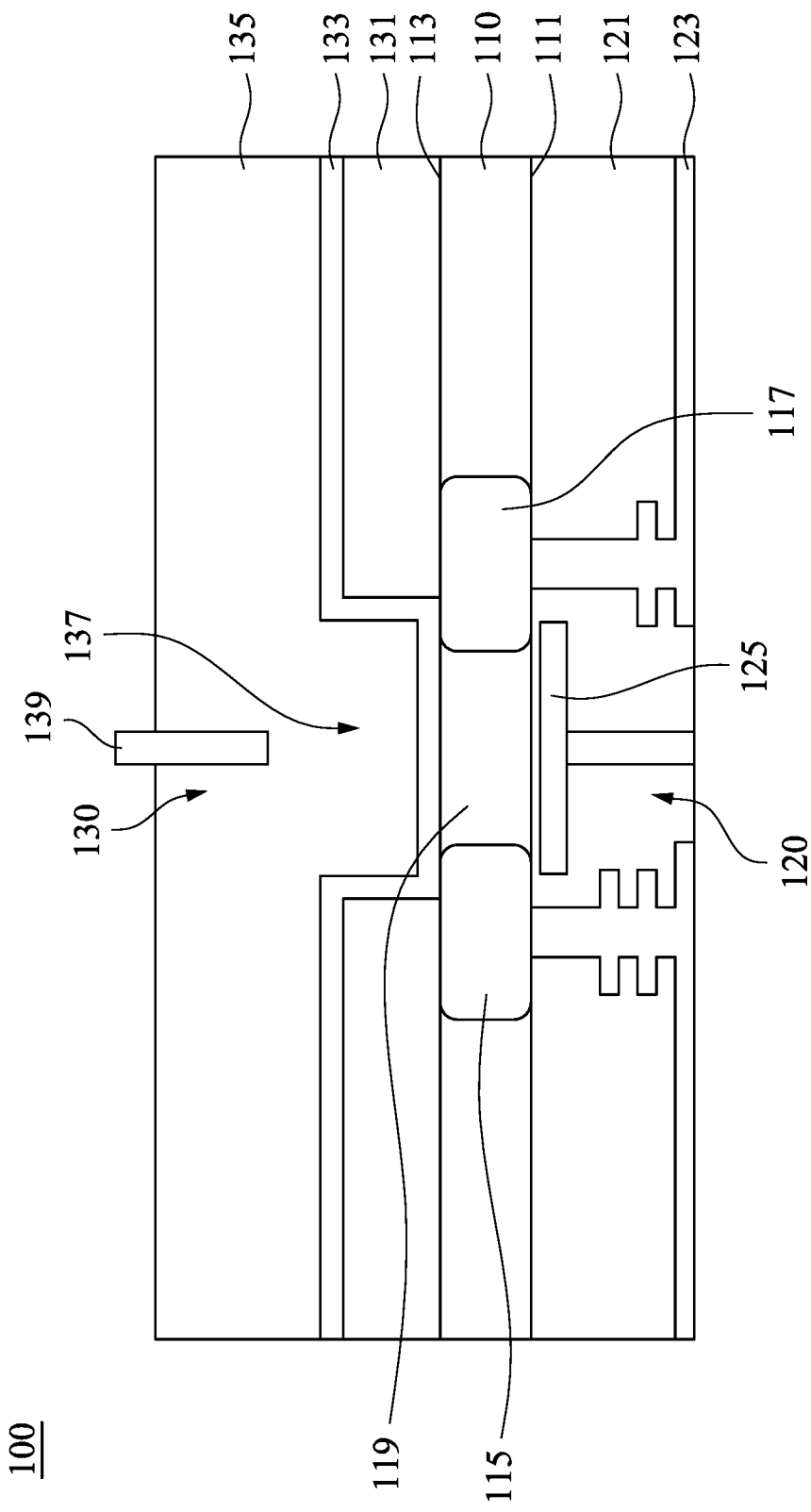
FIG. 1 is a schematic cross-sectional diagram showing a dual gate biologically sensitive field effect transistor (Bio-FET) in accordance with some embodiments of the instant disclosure.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

In a biologically sensitive field effect transistor (BioFET), the gate of a metal-oxide-semiconductor field-effect transistor (MOSFET) is replaced by a bio- or biochemical-compatible layer or a biofunctionalized layer of immobilized probe molecules that act as surface receptors. A BioFET is primarily a field-effect biosensor with a semiconductor transducer, and the gate controls the conductance of the semiconductor between its source and drain contacts.

Typical detection mechanism of BioFETs is the conductance modulation of the transducer resulting from the binding of a target biomolecule to the gate or to a receptor molecule immobilized on the gate. When the target biomolecule binds to the gate or the immobilized receptor, the drain current of the BioFET is changed by the gate potential. This fluctuation in the drain current can be measured, and the bonding between the receptor and the target biomolecule can be identified. A great variety of biomolecules may be used as the gate of the BioFET such as ions, enzymes, antibodies, ligands, receptors, peptides, oligonucleotides, cells of organs, organisms and pieces of tissue. For example, to detect single-stranded deoxyribonucleic acid (ssDNA), the gate of the BioFET is equipped with immobilized complementary ssDNA strands. Also, to detect various proteins such as tumour markers, monoclonal antibodies may be implemented as the gate of the BioFET.

When an electric field is applied across a piece of material, the electrons respond by moving with an average velocity called drift velocity. This phenomenon is known as electron mobility. Conventional BioFET sensors suffer from large accumulative drift effect. The drift effect results from electrical field enhanced ion migration within the gate insulator, and the electrochemical non-equilibrium occurs at the insulator-solution interface. In one example, the drift rate is as high as 36 nA/min under operation mode. The high drift rate may lead to compromising in the sensitivity of the sensor. Many approaches have been used to attenuate drift effect. For example, when a BioFET requires calibration, a test power source is applied to the background, and a current change related to pH value in the solution is detected. A threshold slope (current/time) is measured according to the current change. The signal then undergoes analogue/digital conversion in a CPU, and time drift data is extracted and stored in the memory. This time drift data is used in the calibration when an analyte test is conducted. However, to obtain background time drift data is relatively time consuming, and the collective time drift data results in accumulative deviation. Furthermore, the process requires complex hardware set, for example, the analogue-digital converter, CPU and memory unit.

Another example of conventional BioFET calibration uses a reference FET (REFET) along with the existing BioFET. In contrast to the BioFET, this REFET is non-biologically sensitive. REFET obtains the background voltage of the pH value in the solution along with time, while the Bio-FET obtains the bio-sensitive voltage data alone with time. A differential measurement is then conducted between this pair. In this calibration system, REFET has to be fabricated in additional process, and once the drift effect in the REFET is taken into account, the error range may increase.

Still another example of conventional BioFET calibration system uses pulse-modulated biasing to repeatedly reset vertical electrical field and therefore reduce the drift effect. In this approach, a high-frequency alternating current (AC) biasing is required. As a result, a time discrete sample readout interface has to be designed for interpreting the data.

Please refer to FIG. 1. FIG. 1 shows a dual gate BioFET sensor 100 in accordance with some embodiments of the instant disclosure. The sensor 100 includes a substrate 110, a first control gate 120 and a second control gate 130. It should be understood the number of the first and second control gates is not limited to one. The same system can be applied to multiple control gate structure. For the sake of clarity, only a pair of first and second control gates is shown in the figures. The substrate 110 has a first side 111 and a second side 113 opposite to the first side. The substrate 110 may be a semiconductor substrate (e.g., wafer). The semiconductor substrate may be a silicon substrate. Alternatively, the substrate 110 may include another elementary semiconductor, such as germanium; a compound semiconductor including silicon carbide, gallium arsenic, gallium phosphide, indium phosphide, indium arsenide, and/or indium antimonide; an alloy semiconductor including SiGe, GaAsP, AlInAs, AlGaAs, GaInAs, GaInP, and/or GaInAsP; or combinations thereof. In an embodiment, the substrate 110 is a semiconductor on insulator (SOI) substrate. The substrate may include doped regions, such as p-wells and n-wells.

The source, drain, and/or channel region 115, 117, 119 are formed on an active region of the substrate 110. The FET may be an n-type FET (nFET) or a p-type FET (pFET). For example, the source/drain regions 115, 117 may include n-type dopants or p-type dopants depending on the FET configuration. The first control gate 120 is disposed on the first side 111 of the substrate 110 and includes a gate dielectric layer 121, an interconnect layer 123, a first gate electrode 125, and/or other suitable layers. In an embodiment, the gate electrode 125 is polysilicon. Other exemplary gate electrodes include metal gate electrodes including material such as, Cu, W, Ti, Ta, Cr, Pt, Ag, Au; suitable metallic compounds like TiN, TaN, NiSi, CoSi; combinations thereof; and/or other suitable conductive materials. In an embodiment, the gate dielectric layer 121 is silicon oxide. Other exemplary gate dielectric layer 121 includes silicon nitride, silicon oxynitride, a dielectric with a high dielectric constant (high k), and/or combinations thereof. Examples of high k materials include hafnium silicate, hafnium oxide, zirconium oxide, aluminum oxide, tantalum pentoxide, hafnium dioxide-alumina ($HfO_2Al_2O_3$) alloy, or combinations thereof. The first control gate 120 may be formed using typical CMOS processes such as, photolithography; ion implantation; diffusion; deposition including physical vapor deposition (PVD), metal evaporation or sputtering, chemical vapor deposition (CVD), plasma-enhanced chemical vapor deposition (PECVD), atmospheric pressure chemical vapor deposition (APCVD), low-pressure CVD (LPCVD), high density plasma CVD (HDPCVD), atomic layer deposition (ALD), spin on coating; etching including wet etching, dry etching, and plasma etching; and/or other suitable CMOS processes.

The substrate 110 further includes a buried oxide (BOX) layer 131 formed by a process such as separation by implanted oxygen (SIMOX), and/or other suitable processes. An opening 137 is formed at the second side 113 of the substrate 110. The opening 137 may include a trench formed in one or more layers disposed on the second side 113 of the substrate 110 that includes the first control gate 120. The opening 137 expose a region underlying the first control gate 120 and body structure (e.g., adjacent the channel region 119 of the first control gate 120). In an embodiment, the opening 137 exposes an active region (e.g., silicon active region) underlying the first control gate 120 and active/channel region 119 of the substrate 110. The opening 137 may be formed using suitable photolithography processes to provide a pattern on the substrate and etching process to remove materials from the buried oxide layer 131 until the second side 113 of the substrate 110 is exposed. The etching processes include wet etch, dry etch, plasma etch and/or other suitable processes.

A sensing film 133 is formed conformingly to the BOX 131 and the opening 137. The sensing film 133 is deposited over the sidewalls and bottom of opening 137 and the exposed active region underlying the first control gate 120. The sensing film 133 is compatible to biomolecules or bio-entities binding. For example, the sensing film 133 may provide a binding interface for biomolecules or bio-entities. The sensing film 133 may include a dielectric material, a conductive material, and/or other suitable material for holding a receptor. Exemplary sensing materials include high-k dielectric films, metals, metal oxides, dielectrics, and/or other suitable materials. As a further example, exemplary sensing materials include $HfO_2$, $Ta_2O_5$, Pt, Au, W, Ti, Al, Cu, oxides of such metals, $SiO_2$, $Si_3N_4$, $Al_2O_3$, $TiO_2$, TiN, SnO, $SnO_2$, $SrTiO_3$, $ZrO_2$, $La_2O_3$; and/or other suitable materials. The sensing film 133 may be formed using CMOS processes such as, for example, physical vapor deposition (PVD) (sputtering), chemical vapor deposition (CVD), plasma-enhanced chemical vapor deposition (PECVD), atmospheric pressure chemical vapor deposition (APCVD), low-pressure CVD (LPCVD), high density plasma CVD (HDPCVD), or atomic layer deposition (ALD). In some embodiments, the sensing film 133 may include a plurality of layers. A receptor such as an enzyme, antibody, ligand, peptide, nucleotide, cell of an organ, organism, or piece of tissue is placed on the sensing film 133 for detection of a target biomolecule.

A reference electrode 139 is placed in the analyte solution 135 at the second side 113 of the substrate 110, functioning as the second control gate 130. In some embodiments, the sensing film 133 is exposed to the analyte solution 135, and the reference electrode 139 is immersed in the analyte solution such that the second control gate 130 is a fluidic gate. The second control gate 130 is in Off-state. The analyte solution may be seen as a SOI transistor bulk substrate. That is, the fluidic gate 130 is turned off, while the standard MOS gate 120 functions as in On-state. The surface potential change of the second control gate 130 modulates the threshold voltage ($V_{TH}$) of the first control gate 120 transistor through capacitive coupling. When the gate of the sensor 100 (e.g., the second control gate 130) is triggered by the presence of biomolecule, the sensor 100 will transfer electrons and induce the field effect charging of the first control gate 120, thereby modulating the current (e.g., Ids). The change of the current or threshold voltage ($V_{TH}$) can serve to indicate detection of the relevant biomolecules or bio-entities. Thus, the time drift effect caused by solution charging or large vertical electrical field is greatly reduced as the second control gate 130 is in Off-state. A voltage biasing between the source region 115, 117 and the second control gate 130 is smaller than a threshold voltage of the second control gate 130. More specifically, the threshold voltage of the second control gate 130 is approximately 0.5 V. In conventional dual gate BioFET system, the turn-on voltage of the fluidic gate transistor is much higher than that of the standard MOSFET. Furthermore, because no voltage is applied through the second control gate 130, the required overall voltage remains much lower than a conventional dual gate BioFET. However, because of substrate effect, the threshold voltage of the fluidic gate still exists in trace.

Please refer to FIG. 2A. BioFET sensor 200 is nearly identical to the sensor 100. The first control gate is designated as the bottom gate ($V_{BG}$) 220, and the second control gate is designated as the front gate ($V_{FG}$) 230 in FIG. 2A. In some embodiments, the source/drain regions contain n-type dopant. The channel region 237 is sandwiched between the front gate 230 and the bottom gate 220. In sensor 100, the sensing film 133 is formed on the exposed BOX 131 and the opening 137. In sensor 200, the sensing film 233 is deposited over the entire BOX 131 and undergoes photoresist pattern. The portion over the channel region 237 of the sensing film 233 is protected. Unprotected portions of the sensing film 233 is removed in an etch process. The etch process may involve any known etch process including plasma etch, since the portion susceptible to PID is protected. FIG. 2A shows a sensing film 233 remaining on the respective surface. In FIG. 2A, sensing film 233 is shown only at the bottom surface of opening 137. However, in some embodiments the sidewalls of the opening 137 may also be covered with sensing film 233. The sensing film 233 completely covers the channel region 237 and partially covers the source and drain region 115, 117. The partial coverage of the source and drain region may be adjusted based on the FET design and area requirements for the sensing film 233. In order to prevent unspecified binding of biomolecules on surface other the sensing film 233, a blocking layer or a passivation layer may be deposited. A passivation layer may be silicon nitride, silicon oxide, or other solid-state dielectric layers. A blocking agent, which may be solid or liquid on which a biomolecule cannot bind or has low affinity, may be used in forming passivation layer. One example is hexamethyldisiloxane (HMDS). In another example, a protein such as a Bovine Serum Albumin (BSA) is used as the blocking agent. The blocking layer/passivation layer may be thicker or thinner than the sensing film 233. In some embodiments, the molecule of interest is proton ($H^+$). When protons are received by the receptor on the sensing film 233, the ion-dependent surface potential of the front gate 230 change. The sensor 200 will transfer electrons and induce the field effect charging of the device, thereby modulating the threshold voltage of the bottom gate 220 through capacitive coupling.

As shown in FIG. 2B, a simplified coupling circuitry is depicted. VFG represents the front gate voltage, VBG represents the bottom gate voltage. In between the front and bottom gates, the capacitive coupling goes through the gate oxide (sensing film 233) of the front gate (COX, FG) and crosses the channel region 237 of the substrate 110 (CSi), and before reaching the bottom gate 220, the gate dielectric layer 121 has to be passed. The capacitive coupling principle can be deduced through the following equations:

$$V_{TH,FG} = E_{ref} - \phi_s + \chi_{sol} - \frac{\phi_m}{q} + V_{TH,MOS}$$

$$\Delta V_{TH,BG} = -\frac{C_{OX,FG}}{C_{OX,BG}} \cdot \frac{C_{Si}}{C_{Si} + C_{OX,BG}} \cdot \Delta V_{TH,FG}$$

$$= -\frac{C_{OX,FG}}{C_{OX,BG}} \cdot \frac{C_{Si}}{C_{Si} + C_{OX,BG}} \cdot \Delta \phi_s$$

$V_{TH,FG}$ represents the threshold voltage of the front gate 230, $E_{ref}$ represents the reference electrode potential, $\phi_s$ represents surface potential related to pH, $\chi_{sol}$ is surface dipole potential of the solution, the $\phi_m/q$ comes from semiconductor electron work function, and $V_{TH, MOS}$ represents the threshold voltage of the front gate 230 when it acts as a standard MOSFET device.

FIG. 2C is another schematic view of the sensor 200 circuit layout. Upon receiving the biomolecules, the surface potential of the sensing film 233 changes, and through capacitive coupling, the bottom gate ($V_{BG}$) (e.g., MOS gate) response to the change in the current. D and S represent drain and source regions 115, 117 respectively.

Figure 3B:
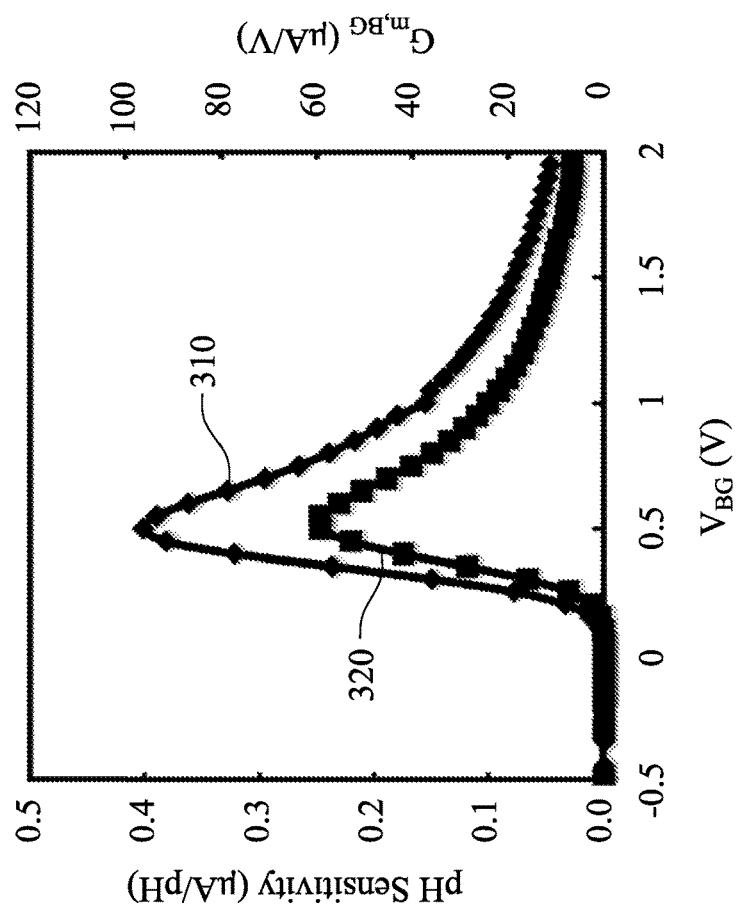
FIG. 3B is a graph showing pH sensitivity and transconductance of back gate in a dual gate biologically sensitive field effect transistor (Bio-FET) in accordance with some embodiments of the instant disclosure.
Figure 3A:
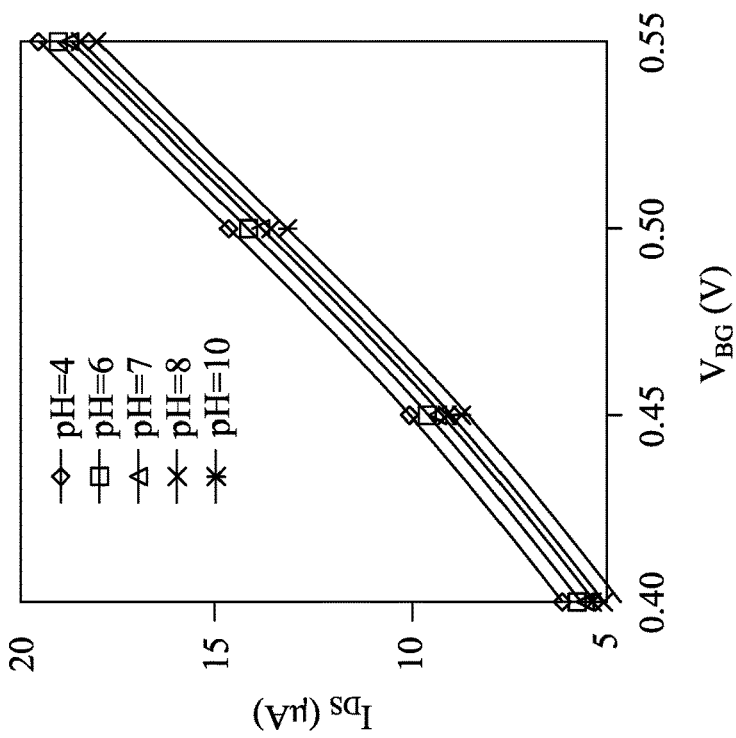
FIG. 3A is a graph showing current sensitivity to pH variation of a dual gate biologically sensitive field effect transistor (Bio-FET) in accordance with some embodiments of the instant disclosure.

The pH value in the sensor 100, 200 has a decided effect to the accuracy of the device. The sensor has dual control gates, but the second control gate is in Off-state, and the first control gate is in On-state. This system allows less threshold voltage interference from the second control gate, which is a fluidic gate usually having larger voltage bias. The circuitry design is simpler without additional circuitry for calibration purpose. Please refer to FIGS. 3A and 3B. FIGS. 3A and 3B show the pH effect to the device voltage. FIG. 3A shows the change of the current (e.g., $I_{DS}$) under different pH conditions, for example, pH 4, 6, 7, 8 and 10. The pH current sensitivity changes in acidic analyte solution or alkali analyte solution. Threshold voltage is heavily influenced by pH variation and hence the change of current ($I_{DS}$).

Attention is now invited to FIG. 3B. Line 310 shows the transconductance of the first control gate (e.g., back gate), and line 320 shows the pH sensitivity, which is derived from change of current over pH value ($\Delta I_{DS}$/pH). The current sensitivity is optimised when the transistor transconductance is in peak. More specifically, when the first control gate has a transconductance approximately 90 μA/V, the current sensitivity reaches approximately 0.25 μA/pH. It suggests an optimisation of the current sensitivity in this dual gate BioFET system where the second control gate (e.g., fluidic gate) is in Off-state.

Figure 4:
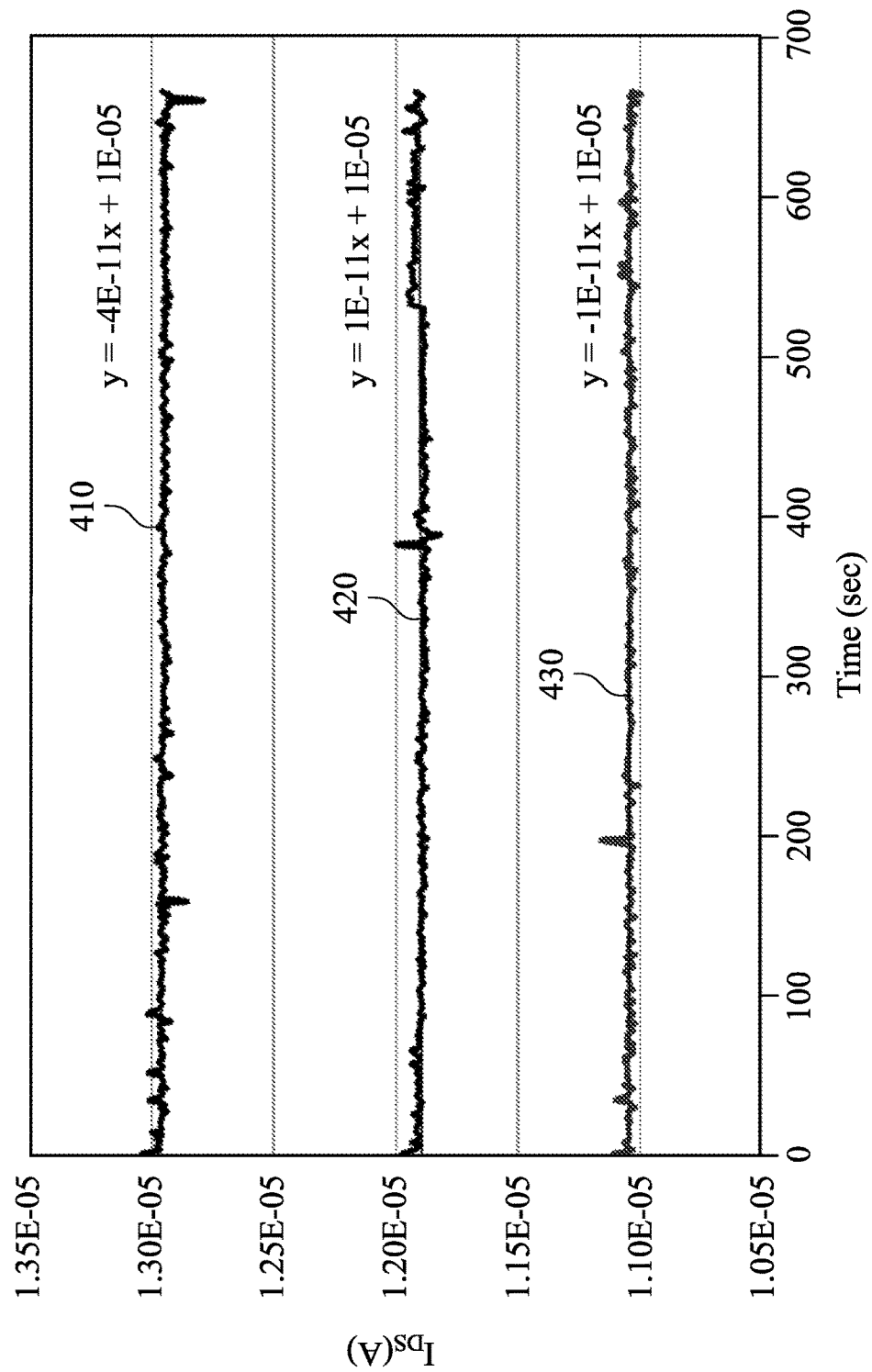
FIG. 4 is a graph showing current drift rate at various pH value of a dual gate biologically sensitive field effect transistor (Bio-FET) in accordance with some embodiments of the instant disclosure.

Attention is now invited to FIG. 4. FIG. 4 is a graph showing change of current against time in second of the first control gate (e.g., MOS gate) at different pH conditions. Line 410 represents the change of current ($I_{DS}$) at pH 4, line 420 represents the change of current at pH 7, and line 430 represents the change of current at pH 10. The linear equation indicates the slope of the drift rate in each case. Please refer to Table 1.

TABLE 1

| | pH | | |
|---|---|---|---|
| | 4 | 7 | 10 |
| Average Current | 12.9441E−6 | 11.9125E−6 | 11.0429E−6 |
| Sensitivity (μA/pH) | 0.344 | 0.290 | 0.290 |
| Drift Rate (μA/s) | −4.00E−5 | 1.00E−5 | −1.00E−5 |
| Drift Rate (pH/s) | −1.16E−4 | 2.91E−5 | −2.91E−5 |

According to FIG. 4 in conjunction with Table 1, the drift rate is level, nearly constant along the time course. Directional drift, either positive or negative cannot be observed under different pH value. In comparison with conventional single-gate BioFET sensing system, the drift rate reduction shows a reduction ranging from 20 (at pH 4) to 50 folds (at pH 7) in this dual gate BioFET system. The drift effect is greatly reduced due to the withdrawal of current from the second control gate (e.g., fluidic gate).

A readout interface is designed for the dual gate BioFET. Conventional biosensors have, for example, single-gate FET using constant-voltage constant-current (CVCC) structure to extract threshold variation ($\Delta N_{TH}$) of the BioFET. In this configuration, a large circuitry is required with at least 2 operational amplifiers (OP AMP), 1 resistor and 2 current sources. The body effect has great impact on the current source drifting, and therefore, due to the size and accuracy it is not suitable in sensory array. Another example involves a differential pair of ISFET/MOSFET with indirect voltage feedback loop to MOSFET to extract threshold voltage variation of the BioFET ($\Delta V_{TH,BIO}$). The Drain/source voltage varies according to the bio-signals from the ISFET, and the current source also suffers from body effect. The voltage readout depends on two sets of FETs, and therefore, deviation adds on to the result. Still another example of conventional readout interface employs simpler circuitry with 1 operational amplifier and 1 resistor and direct voltage feedback to the reference electrode in solution to extract signals. Although body effect may reduce in this configuration, the output voltage is connected to the reference electrode in the solution, and therefore, the direct voltage feedback can only be used for a single one sensor. This configuration has constant drain current and drain voltage but is not suitable in a sensor array because of structural hindrance.

Figure 5:
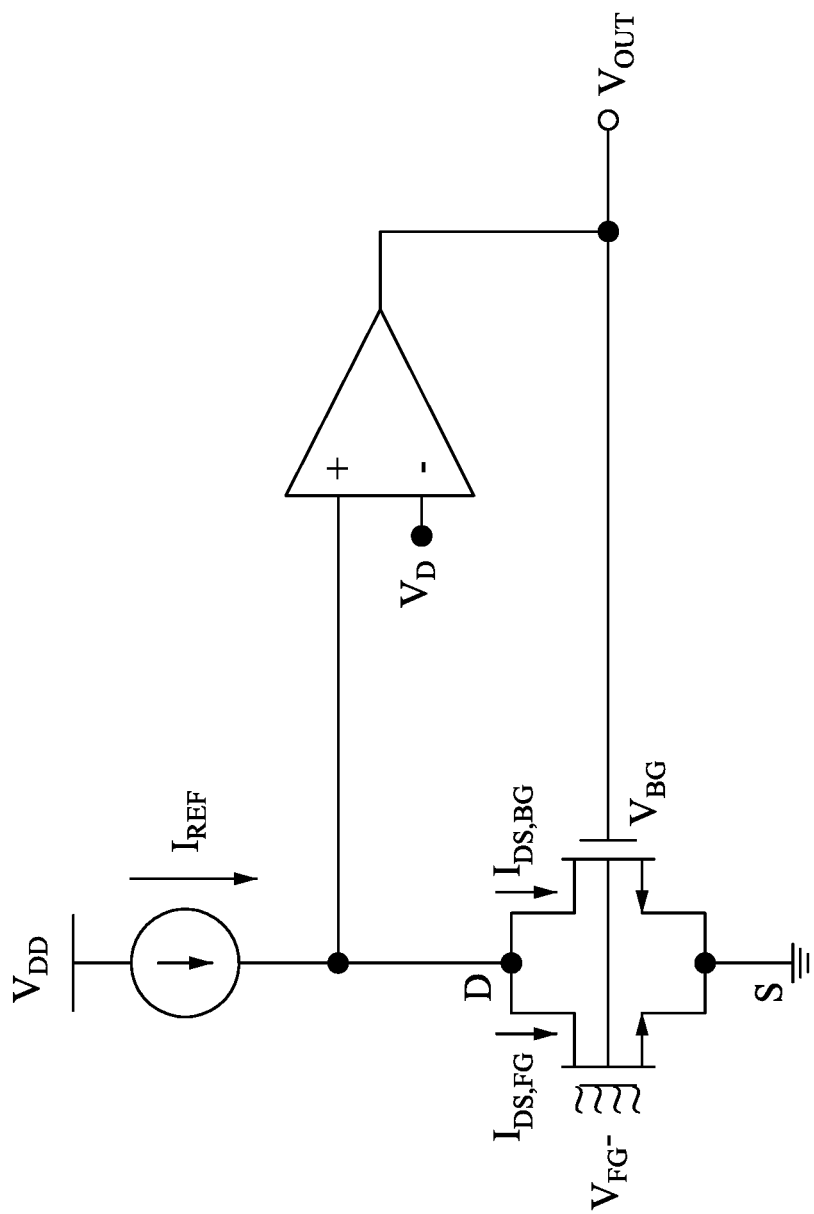
FIG. 5 is a schematic diagram showing a simplified circuit layout of a dual gate biologically sensitive field effect transistor (Bio-FET) in accordance with some embodiments of the instant disclosure.

The BioFET sensor 100, 200 may be implemented in a readout interface of a sensor array, and from the series of BioFET, the threshold voltage may be efficiently collected, and at the same time sensitivity is not compromised. BioFET sensor 100, 200 may be replaced by, for example, a single gate BioFET having FET counterparts. It should be noted that all the drain terminals of the FETs are connected together, and all the source terminals thereof are connected together. Attention is now invited to FIG. 5, illustrating a simplified schematic diagram of BioFET circuitry in accordance with some embodiments of the instant disclosure. $V_{BG}$ represents the first control gate (e.g., back gate), $V_{FG}$ represents the second control gate (e.g., front gate), D represents the drain, and S represents the source. A reference current $I_{REF}$ is connected to the drain D. The reference current may be replaced by a resistor between the drain and a constant voltage source (e.g., $V_{DD}$). An operational amplifier is arranged in the configuration to lock the drain voltage. The operational amplifier (i.e., feedback amplifier) includes a first input terminal, a second input terminal and an output terminal. The first input terminal is connected to the drain terminal D of the BioFET, and the second input terminal is connected to the reference voltage $V_D$. The output terminal is connected to one of the control gate that is not a fluidic gate (e.g., first control gate). The readout interface also includes a constant input terminal connected to the drain terminal. Upon operation, a constant current is supplied to the constant input terminal as a constant reference source.

In some of the embodiments, the second control gate is in On-state and the first control gate is in Off-state. When the sensing film of the BioFET receives molecule of interest, a surface potential change is initialised on the sensing film of the second control gate. Through capacitance coupling, the voltage change at the first control gate, which is at Off-state, will induce coupling effect to the second control gate. The variation of threshold voltage ($\Delta V_{TH}$ (pH)) occurs at the second control gate is affected by the pH value. Also, the voltage change of the first control gate ($\Delta V_{BG}$) results in a variation of threshold voltage $\Delta V_{TH}$ ($V_{BG}$) at the second control gate as well. The $\Delta V_{TH}$ of the second control gate by the pH value is therefore cancelled out by the $\Delta V_{TH}$ caused by the first control gates due to coupling effect. As a result, the $\Delta V_{OUT}$, which is equal to $\Delta V_{BG}$, is larger than $\Delta V_{TH}$ (pH), resulting in an amplification gain larger than 1. The thickness of the oxide layer has an influence on the coupling effect because, the oxide capacitance shown in FIG. 2B, is highly depend on the thickness of the oxide layer. It should be noted that the circuitry shown in FIG. 5 may be employed to a dual MOSFET structure or an ISFET along with a MOSFET.

Figure 6:
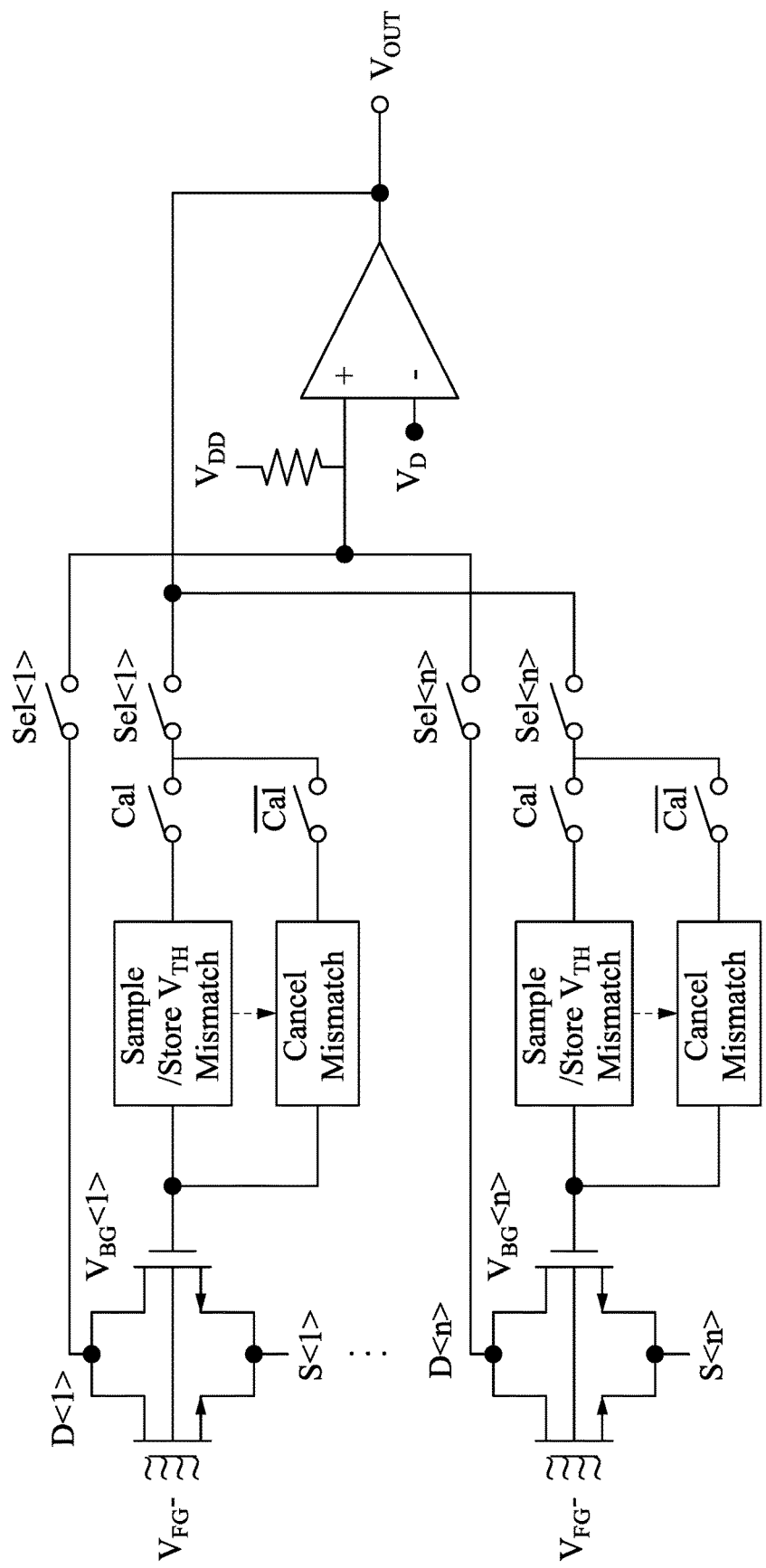
FIG. 6 is a schematic diagram showing a simplified circuit layout of a series of dual gate biologically sensitive field effect transistors (Bio-FET) in accordance with some embodiments of the instant disclosure.

FIG. 6 shows an implementation of the BioFET in a sensor array. Individual threshold voltage goes through mismatch calibration before performing standard sensing procedure. In the calibration mode, the sampling loop is on, while the cancel mismatch loop is off. The data of initial threshold voltage mismatch of each pixel is then stored in a threshold voltage storage unit. The sensor array includes a plurality of sensor units, and the mismatch compensation process goes through each of the sensor units for a collective result. Therefore, in the mismatch calibration process, a switching between each of the sensor units occurs such that all the mismatch data from the sensor units are collected. More specifically, as shown in FIG. 6, a sensor array may include more than one sensor unit. The mismatch calibration goes through 1-n of the sensor units, and the system switches from Sel<1>, Sel<2> . . . to Sel<n> so as to collect all the mismatch data. Detail mechanism of the calibration process is elaborated in FIGS. 7A and 7B. In the sensing mode, the sampling loop is off, while the cancel mismatch loop is on, and normal sensing operation is performed.

Figure 7A:
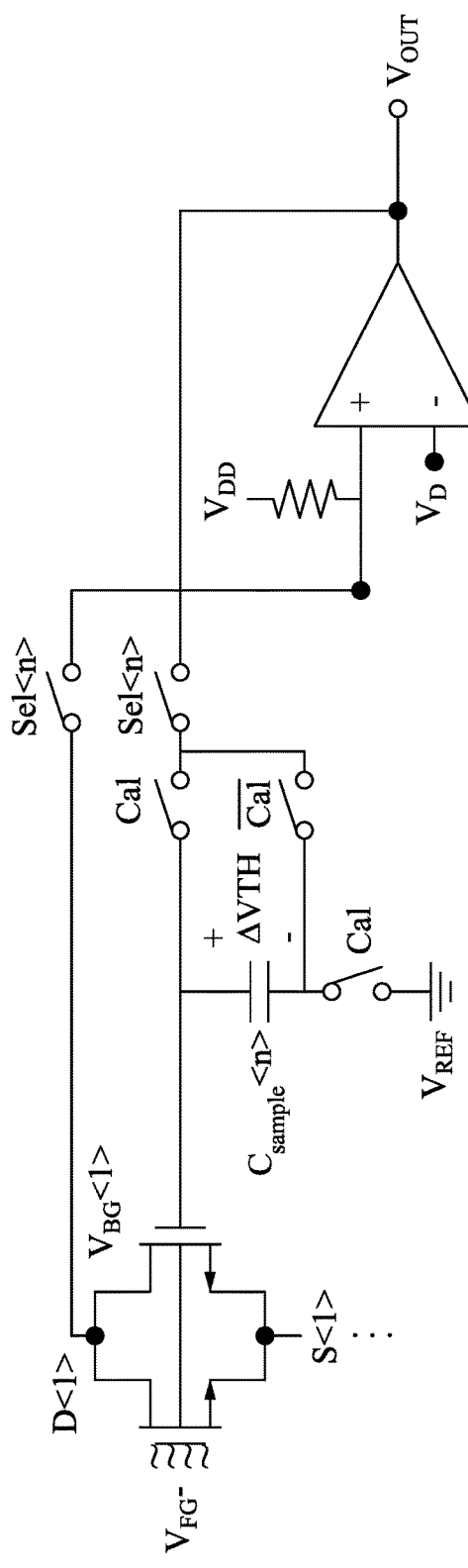
FIG. 7A is a schematic diagram showing a detailed analogue circuit layout of a dual gate biologically sensitive field effect transistor (Bio-FET) in accordance with some embodiments of the instant disclosure.
Figure 7B:
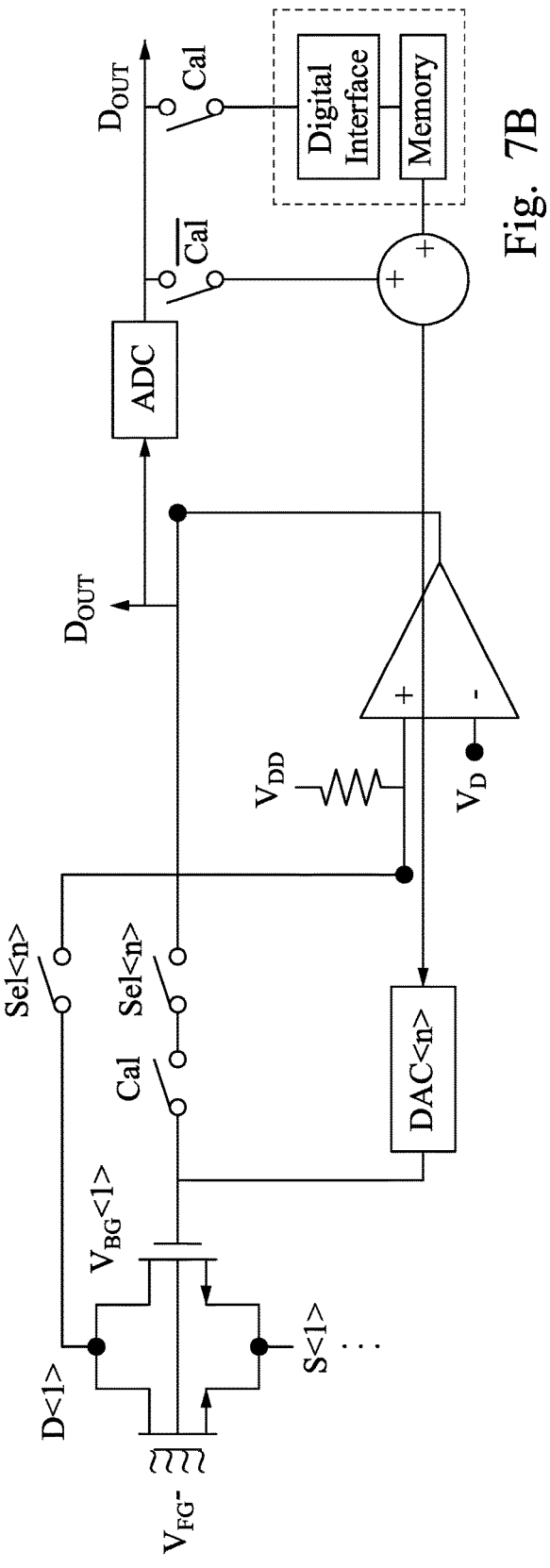
FIG. 7B is a schematic diagram showing a detailed digital circuit layout of a dual gate biologically sensitive field effect transistor (Bio-FET) in accordance with some embodiments of the instant disclosure.

Attention is now invited to FIG. 7A. FIG. 7A shows a schematic view of the analogue design of the sampling loop and the cancel mismatch loop in accordance with some embodiments of the instant disclosure. When the sensor undergoes mismatch calibration, a first signal (voltage or current) goes through the sampling loop. That is, the first signal goes through the Cal. Next, a mismatch of each of the sensor unit in the sensor array is estimated and stored. The mismatch data is generated according to the first signal from the sampling loop. Subsequently, a mismatch compensation of each of the sensor unit is performed, and a second signal goes through the cancel mismatch loop. As a result, the initial threshold voltage mismatch of each sensor unit in the sensor array is corrected. FIG. 7B shows a digital design of the sampling loop and the cancel mismatch loop in accordance with some embodiments of the instant disclosure. When the mismatch calibration takes place, a signal goes through the Cal path, where an analogue to digital converter is present and the threshold voltage mismatch is stored in the memory through digital interface. When the sensor is under sensing mode, a signal goes through the other path, where a digital to analogue converter is encountered and the data is output after it is processed according to the threshold voltage data stored in the memory.

Figure 8:
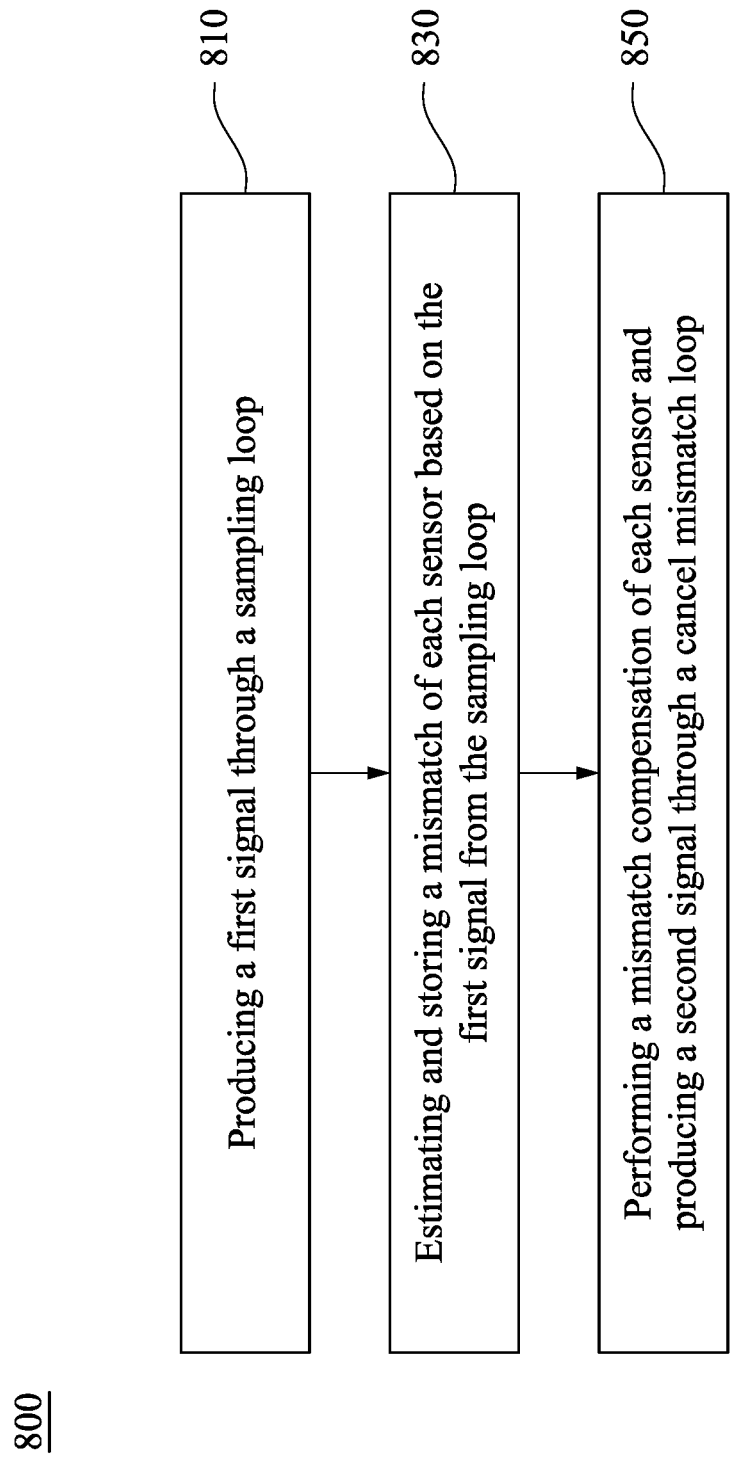
FIG. 8 is a flow chart showing a method of threshold mismatch calibration for sensory array in accordance with some embodiments of the instant disclosure.

The instant disclosure utilizes dual gate structure and allows the capacitive coupling effect takes place. One of the gate is in Off-state, and therefore the solution biasing voltage is reduced, and the time drifting effect is minimized. The detection resolution of the device is enhanced because more variation is removed or attenuated from the structural design. When implementing the structure to a readout interface, the amplification gain may be greater than 1. FIG. 8 shows the process of the calibration in the sensor array, where each sensor includes two gates. At operation 810, a first signal is produced and goes through a sampling loop. The first signal may be a current or a voltage. At operation 830, a mismatch of each of the sensor unit is estimated and stored according to the first signal from the sampling loop. In a sensor array, mismatch data of each and every sensor unit are collected. The mismatch data are stored in the corresponding storage unit in each sensor unit. At operation 850, a mismatch compensation of each sensor unit is performed, and a second signal is produced through a cancel mismatch loop so as to calibrate the sensor array.

In one aspect of the instant disclosure, a biologically sensitive field effect transistor includes a substrate, a first control gate and a second control gate. The substrate has a first side and a second side opposite to the first side, a source region and a drain region. The first control gate is disposed on the first side of the substrate. The second control gate is disposed on the second side of the substrate. The second control gate includes a sensing film disposed on the second side of the substrate. A voltage biasing between the source region and the second control gate is smaller than a threshold voltage of the second control gate.

In another aspect of the instant disclosure a dual gate field effect transistor readout interface includes a field effect transistor including at least two gate terminals, a drain terminal and a source terminal. The readout interface further includes a feedback amplifier comprising a first input terminal connected to the drain terminal, a second input terminal biased at a reference voltage and an output terminal connected to one of the control gate.

In still another aspect of the instant disclosure a method includes producing a first signal through a sampling loop, estimating and storing a mismatch of each unit based on the first signal from the sampling loop, and performing mismatch compensation and produce a second signal through a cancel mismatch loop.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein.

What is claimed is:

1. A sensing circuit, comprising:
   a biologically sensitive field effect transistor (BioFET) comprising:
   a substrate having a first side and a second side opposite to the first side, the substrate having a source region and a drain region,
   a first control gate disposed on the first side of the substrate, and
   a second control gate disposed on the second side of the substrate, the second control gate including a sensing film disposed on the second side of the substrate; and
   a storage unit coupled to the first control gate and configured to store a difference between a first threshold voltage of the first control gate and a second threshold voltage of the second control gate.

2. The sensing circuit of claim 1, wherein the first control gate comprises a gate dielectric layer and an interconnect layer disposed in the gate dielectric layer.

3. The sensing circuit of claim 1, wherein the second threshold voltage of the second control gate is smaller than 0.5 V.

4. The sensing circuit of claim 1, wherein the BioFET further comprises a buried oxide layer disposed on the second side of the substrate, wherein an opening is formed in the buried oxide layer to expose the second side of the substrate and aligned with the first control gate.

5. The sensing circuit of claim 4, wherein the sensing film is conformingly disposed on the buried oxide layer and lining the exposed second side of the substrate.

6. The sensing circuit of claim 1, wherein the first control gate and the second control gate have the same source region and drain region.

7. The sensing circuit of claim 1, wherein the first control gate is a metal-oxide semiconductor control gate, and the second control gate is a fluidic control gate.

8. The sensing circuit of claim 7, wherein the fluidic control gate comprises an analyte solution and a reference electrode disposed in the analyte solution.

9. A sensing circuit, comprising:
   a biologically sensitive field effect transistor (BioFET) comprising:
   a substrate having a first side and a second side opposite to the first side, the substrate having a channel region, a source region, and a drain region,
   a first control gate disposed on the first side of the substrate,
   a buried oxide layer disposed on the second side of the substrate, wherein an opening is formed in the buried oxide layer to expose the second side of the substrate, and
   a second control gate disposed on the second side of the substrate, wherein the second control gate comprises a sensing film disposed on a bottom surface of the opening; and
   a storage unit coupled to the first control gate and configured to store a difference between a first threshold voltage of the first control gate and a second threshold voltage of the second control gate.

10. The sensing circuit of claim 9, wherein the sensing film is disposed only on the bottom surface of the opening.

11. The sensing circuit of claim 9, wherein the sensing film is disposed on sidewalls of the opening.

12. The sensing circuit of claim 9, wherein the sensing film completely covers the channel region and partially covers the source region and the drain region.

13. The sensing circuit of claim 9, wherein the first control gate comprises a gate dielectric layer and an interconnect layer disposed in the gate dielectric layer.

14. The sensing circuit of claim 9, wherein the threshold voltage of the second control gate is smaller than 0.5 V.

15. The sensing circuit of claim 9, wherein the threshold voltage of the second control gate is about 0.5 V.

16. The sensing circuit of claim 9, wherein the first control gate and the second control gate have the same source region and drain region.

17. The sensing circuit of claim 9, wherein the first control gate is a metal-oxide semiconductor control gate, and the second control gate is a fluidic control gate.

18. The sensing circuit of claim 17, wherein the fluidic control gate comprises an analyte solution and a reference electrode disposed in the analyte solution.

19. A method for operating a transistor, comprising:

providing the transistor, wherein the transistor comprises:

a substrate having a first side and a second side opposite to the first side, the substrate having a channel region, a source region, and a drain region, a first control gate disposed on the first side of the substrate, and a second control gate disposed on the second side of the substrate, the second control gate including a sensing film disposed on the second side of the substrate; and applying a bias voltage between the source region and the second control gate, wherein the bias voltage is smaller than a threshold voltage of the second control gate.

20. The method of claim 19, wherein the threshold voltage of the second control gate is about 0.5 V.

* * * * *